US011291868B2

(12) United States Patent
Elliott et al.

(10) Patent No.: US 11,291,868 B2
(45) Date of Patent: Apr. 5, 2022

(54) PULSE SATURATION OXYGEN DELIVERY SYSTEM AND METHOD

(71) Applicant: B/E Aerospace, Inc., Wellington, FL (US)

(72) Inventors: Andrew Elliott, Shawnee, KS (US); Mrinal Nagrecha, Wichita, KS (US); Detlev Degenhardt, Stockelsdorf (DE)

(73) Assignee: B/E Aerospace, Inc., Winston Salem, NC (US)

( * ) Notice: Subject to any disclaimer, the term of this patent is extended or adjusted under 35 U.S.C. 154(b) by 1122 days.

(21) Appl. No.: 15/192,943

(22) Filed: Jun. 24, 2016

(65) Prior Publication Data
US 2016/0303405 A1 Oct. 20, 2016

Related U.S. Application Data

(63) Continuation-in-part of application No. 14/573,998, filed on Dec. 17, 2014, now Pat. No. 10,869,987.
(Continued)

(51) Int. Cl.
*A62B 7/14* (2006.01)
*A62B 18/02* (2006.01)
(Continued)

(52) U.S. Cl.
CPC ............... *A62B 7/14* (2013.01); *A61B 5/024* (2013.01); *A61B 5/0816* (2013.01); *A61B 5/14542* (2013.01); *A61M 16/0051* (2013.01); *A61M 16/024* (2017.08); *A61M 16/1005* (2014.02); *A61M 16/125* (2014.02); *A62B 9/006* (2013.01);
(Continued)

(58) Field of Classification Search
CPC .......... A62B 7/14; A62B 9/006; A62B 18/02; A62B 18/025; A62B 25/005; A61B 5/14542
See application file for complete search history.

(56) References Cited

U.S. PATENT DOCUMENTS 5,365,922 A * 11/1994 Raemer ................ A61B 5/0833
128/202.22
5,664,566 A * 9/1997 McDonald ............. A62B 18/02
128/205.25
(Continued)

FOREIGN PATENT DOCUMENTS

CN 103415325 A 11/2013
WO WO-99/04841 A1 2/1999

OTHER PUBLICATIONS

Office Action issued in Canadian Patent Application No. 2933599 dated Mar. 5, 2018. 4 pages.
(Continued)

*Primary Examiner* — Valerie L Woodward
(74) *Attorney, Agent, or Firm* — Locke Lord LLP; Joshua L. Jones; Gabrielle L. Gelozin

(57) ABSTRACT

In a preferred embodiment, systems and methods for delivering oxygen to a passenger of an aircraft via an oxygen mask having one or more sensors involve analyzing blood oxygen saturation measurements from the sensor(s) to determine a current oxygen saturation level, determining the current oxygen saturation level is insufficient, and adjusting an oxygen flow rate to the mask to compensate for the current blood oxygen saturation level.

16 Claims, 7 Drawing Sheets

Related U.S. Application Data

(60) Provisional application No. 61/919,007, filed on Dec. 20, 2013.

(51) Int. Cl.
*A62B 18/08* (2006.01)
*A61B 5/145* (2006.01)
*A61B 5/024* (2006.01)
*A61B 5/08* (2006.01)
*A62B 9/00* (2006.01)
*A62B 18/10* (2006.01)
*A61M 16/12* (2006.01)
*A61M 16/10* (2006.01)
*A61M 16/00* (2006.01)

(52) U.S. Cl.
CPC .......... *A62B 18/025* (2013.01); *A62B 18/084* (2013.01); *A62B 18/10* (2013.01); *A61M 16/101* (2014.02); *A61M 2202/0208* (2013.01); *A61M 2205/502* (2013.01); *A61M 2205/587* (2013.01); *A61M 2230/04* (2013.01); *A61M 2230/205* (2013.01); *A61M 2230/432* (2013.01)

(56) References Cited

U.S. PATENT DOCUMENTS

| | | | |
|---|---|---|---|
| 6,186,142 B1 | 2/2001 | Schmidt et al. | |
| 6,401,714 B1* | 6/2002 | Giorgini | A62B 7/02 128/202.22 |
| 6,510,331 B1* | 1/2003 | Williams | A61B 5/14542 600/323 |
| 7,246,620 B2 | 7/2007 | Conroy, Jr. | |
| 7,278,421 B2* | 10/2007 | Hannah | A62B 18/08 128/201.12 |
| 7,383,105 B2 | 6/2008 | Conroy, Jr. | |
| 7,784,463 B2 | 8/2010 | Cannon | |
| 8,028,700 B2 | 10/2011 | Hannah | |
| 8,584,674 B1 | 11/2013 | Poliard | |
| 2001/0039951 A1* | 11/2001 | Strickland, Jr. | A61M 16/12 128/204.22 |
| 2002/0139368 A1* | 10/2002 | Bachinski | A61M 16/06 128/204.23 |
| 2002/0195105 A1* | 12/2002 | Blue | A61M 16/00 128/204.21 |
| 2004/0163648 A1* | 8/2004 | Burton | A61B 5/04085 128/204.21 |
| 2005/0103342 A1* | 5/2005 | Jorczak | A61M 16/0672 128/205.24 |
| 2006/0011199 A1* | 1/2006 | Rashad | A61M 16/0666 128/204.23 |
| 2006/0213519 A1* | 9/2006 | Schmidt | A61M 16/026 128/204.23 |
| 2008/0000480 A1 | 1/2008 | Cannon | |
| 2009/0301489 A1* | 12/2009 | Bloch | A62B 7/14 128/204.23 |
| 2010/0192952 A1 | 8/2010 | Melker et al. | |
| 2011/0197891 A1* | 8/2011 | Sanders | A62B 9/04 128/205.22 |
| 2012/0160244 A1* | 6/2012 | Sharma HK | A61M 16/0051 128/204.23 |
| 2013/0152933 A1 | 6/2013 | Lischer et al. | |
| 2013/0306073 A1* | 11/2013 | Fromage | A62B 7/14 128/204.22 |
| 2015/0174359 A1 | 6/2015 | Elliott et al. | |
| 2015/0320953 A1* | 11/2015 | Acker | A61M 16/12 128/203.14 |

OTHER PUBLICATIONS

Office Action issued in European Patent Application No. 14825233.1 dated Mar. 28, 2018. 10 pages.

Office Action on Canadian Patent Application No. 2,933,599 dated Jul. 10, 2017. 4 pages.

Office Action on U.S. Appl. No. 14/573,998 dated Dec. 18, 2017. 19 pages.

Benaron, David A. et al.; "Continuous, Noninvasive, and Localized Microvascular Tissue Oximetry Using Visible Light Spectroscopy"; Jun. 2004; Anesthesiology; V 100, No. 6; pp. 1469-1475.

Non-Final Office Action on U.S. Appl. No. 14/573,998, dated May 5, 2017, 20 pages.

Third Office Action issued in CN Application No. 2014800696073 dated Jul. 11, 2019. 28 pages.

International Search Report dated Aug. 11, 2015 in PCT/US2014/071178, published as WO 2015/095532 dated Jun. 25, 2015, 6 pages.

Second Office Action on Chinese Application No. 201480069607.3 dated Feb. 1, 2019. 10 pages.

Final Office Action on U.S. Appl. No. 14/573,998 dated Apr. 24, 2019. 22 pages.

First Office Action on Chinese Application No. 201480069607.3 dated Jul. 11, 2018. 15 pages.

Non-Final Office Action on U.S. Appl. No. 14/573,998 dated Aug. 9, 2018. 20 pages.

Office Action on Canadian patent application No. 2933599 dated Sep. 25, 2018. 4 pages.

Decision of Rejection issued in CN Application No. 2014800696073 dated Mar. 4, 2020. 10 pages.

\* cited by examiner

PULSE SATURATION OXYGEN DELIVERY SYSTEM AND METHOD

CROSS REFERENCES TO RELATED APPLICATIONS

This application is a continuation in part of U.S. application Ser. No. 14/573,998 filed Dec. 17, 2014 which claims priority from U.S. application Ser. No. 61/919,007, filed Dec. 20, 2013, the contents of both which are incorporated by reference in their entirety.

BACKGROUND

Emergency oxygen supply systems are commonly installed on aircraft for the purpose of supplying oxygen to passengers upon loss of cabin pressure at altitudes above about 15,000 feet. Emergency systems of this type typically include a face mask adapted to fit over the mouth and nose of the passenger when released from an overhead storage compartment. The face mask is connected to an onboard oxygen reserve that can distribute oxygen under low pressure to the passengers. The supplemental oxygen delivered to the mask increases the passenger's blood oxygen saturation level beyond what would be experienced if ambient air were breathed at the prevailing cabin pressure altitude condition. The flow of oxygen provided by the oxygen reserve is estimated to be sufficient to sustain all passengers until cabin pressure is reestablished or until a lower, safer altitude can be reached.

In some emergency oxygen delivery systems, the face mask has an attached reservoir bag into which a flow of oxygen is directed upon deployment of the system and upon activation of the individual face mask via a pull cord. The oxygen is supplied at a constant rate that is calculated to accommodate a worst case scenario, namely to satisfy the need of a passenger with a significantly larger than average tidal volume who is breathing at a faster than average respiration rate when cabin pressure is lost at maximum cruising altitude. In a typical breathing mask, a total of three valves serve to coordinate flows between the bag and the mask, and between the mask and the surroundings. An inhalation valve serves to confine the oxygen flowing into the bag to the bag while the passenger is exhaling as well as during the post-expiratory pause, while preventing any reverse flow from the mask into the bag. When the passenger inhales, the inhalation valve opens to allow for the inhalation of the oxygen that has accumulated in the bag. Upon depletion of the accumulated oxygen, the dilution valve opens to allow cabin air to be drawn into the mask. The continuing flow of oxygen into the bag and through the open inhalation valve into the mask is thereby diluted by the cabin air that is inhaled during the balance of the inhalation phase. During exhalation, the exhalation valve opens to allow a free flow from the mask into the surroundings while the inhalation valve closes to prevent flow from the mask back into the bag. All three valves remain closed during the post-expiratory pause while oxygen continues to flow into the reservoir bag.

U.S. patent application Ser. No. 11/853,493 to Cannon, entitled "Oxygen Conservation System for Commercial Aircraft" and filed Sep. 11, 2007 described a system for improving the rate of oxygen consumption on an aircraft emergency oxygen system. The improved efficiency is achieved by a reduction in the rate of oxygen consumption by adjusting the allotment of oxygen to each individual passenger as function of such passenger's actual demand, inducing the passenger to more efficiently use such allotment. More particularly, allotment is adjusted as a function of each passenger's respiration rate wherein faster breathing results in a faster delivery rate of the passenger's oxygen allotments. More efficient use of the delivered oxygen is induced by timing the delivery of oxygen so that it is inhaled into the most absorption efficient region of the lung and by limiting the volume of the delivered oxygen so as to approximately coincide with the volume of that region of the lung. Cabin air is relied upon to fulfill the balance of the passenger's respiratory volume.

SUMMARY

In one embodiment, a pulse saturation oxygen delivery (PSOD) system for pressurized aircraft utilizing one or more sensors configured to determine a wearer's blood oxygen saturation ($SpO_2$) level in order to deliver oxygen to the wearer through a mask, based on their SpO2 level. The PSOD system can improve efficiency of delivering oxygen to the wearer by intermittently releasing the oxygen using a pulse volume regulator or a continuous flow regulator, based on a wearer's oxygen need. The PSOD system includes a controller configured to monitor one or more sensors configured to determine a wearer's oxygen need and control a regulator to vary an amount of oxygen an oxygen source needs to supply to meet their need.

Other features and advantages of the present invention will become more apparent from the following detailed description of the preferred embodiments in conjunction with the accompanying drawing, which illustrates by way of example the operation of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF ILLUSTRATIVE EMBODIMENTS

Figure 1A:
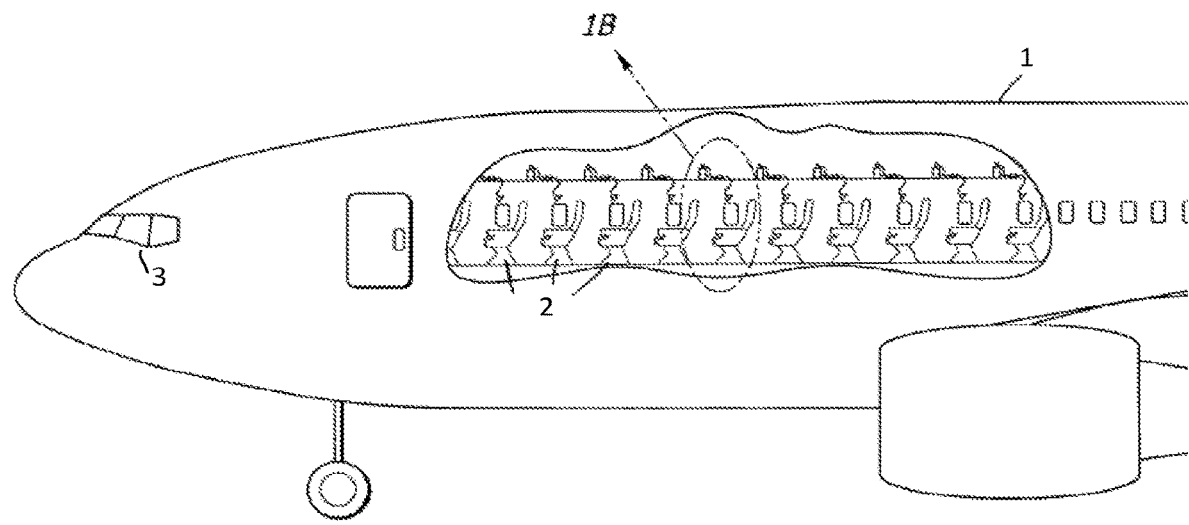
FIG. 1A illustrates an aircraft, partially cut-away, showing a number of passenger seats and a location of an pulse saturation oxygen delivery system according to an example.

Referring now to the drawings, wherein like reference numerals designate identical or corresponding parts throughout the several views.

FIG. 1A illustrates an aircraft 1, partially cut-away, showing a number of passenger seats 1, a location of pilot seat 3, and a location of a pulse saturation oxygen delivery (PSOD) system 100 according to an example.

Figure 1B:
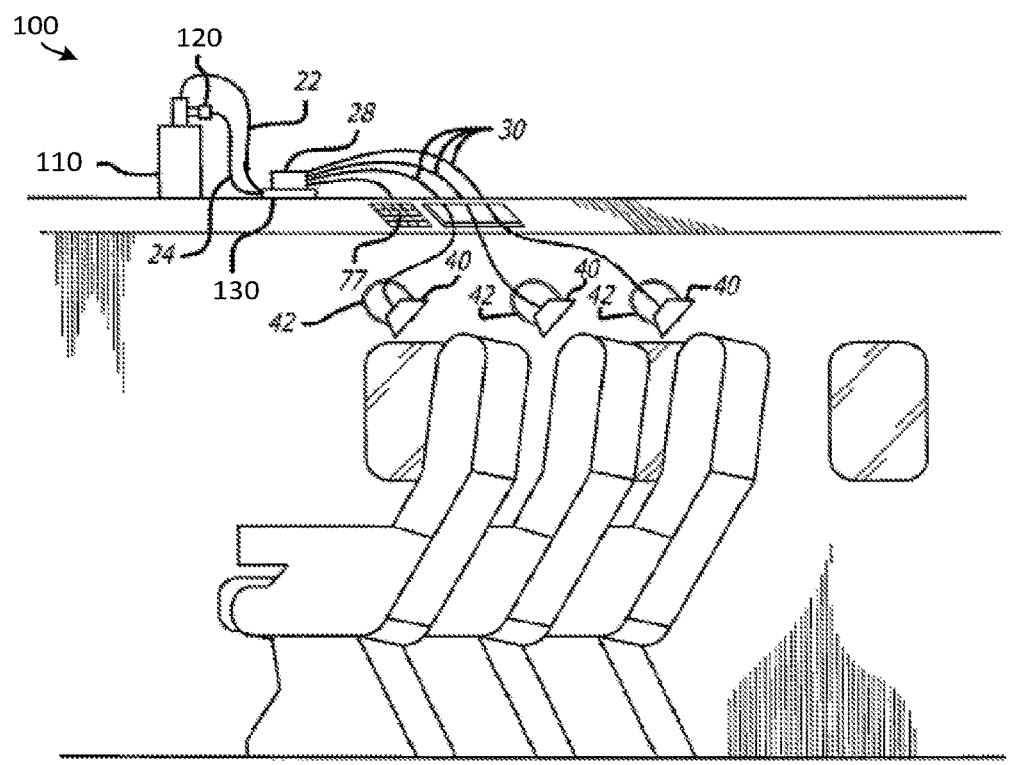
FIG. 1B is a perspective view of the pulse saturation oxygen delivery system of FIG. 1A according to an example.

FIG. 1B illustrates a PSOD system 100 including an oxygen source 110 which is connected to a controller 130 electrically via cabling 22 and also with a flow tube 24 that couples to a pressure reducer/regulator 120 according to an example. Examples of pressure reducer/regulator 120 include a continuous flow regulator 322, a pulse volume regulator 324, and an integrated regulator 220 in a mask (See FIG. 2D).

In an example, the controller 130 can be configured to control the flow of oxygen to an oxygen flow control device 28 to which multiple masks 40 are connected, controlling the oxygen flow for each mask individually. Examples of an oxygen source 110 can include an oxygen cylinder/tank 312, an oxygen concentrator 314, and an oxygen source with an integrated pressure reducer 316 (See FIG. 3C).

Figure 3A:
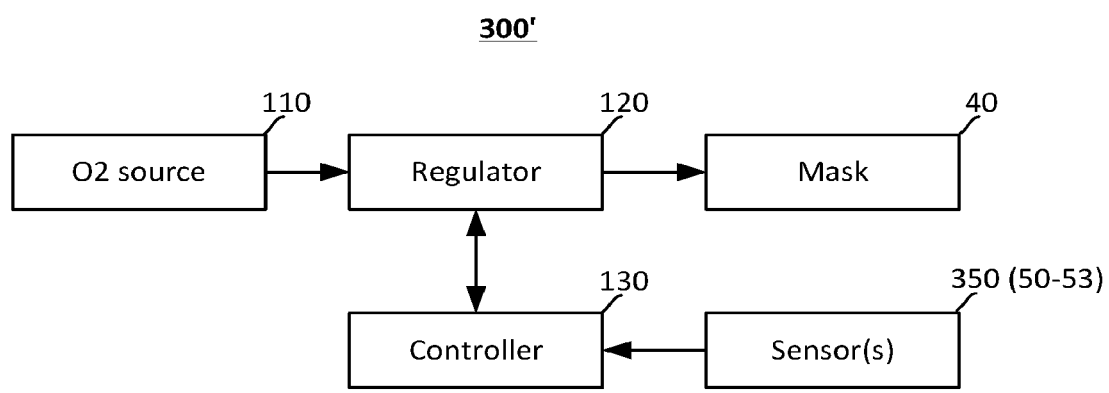
FIG. 3A is a schematic diagram of a pulse saturation oxygen delivery system including an oxygen source, a regulator, a controller, a mask and a sensor according to an example.

FIG. 3A is a schematic diagram of a pulse saturation oxygen delivery system 300' including the oxygen source 110, a regulator 120, a controller 130, a mask 40, and one or more sensors according to an example.

Mask

Figure 2A:
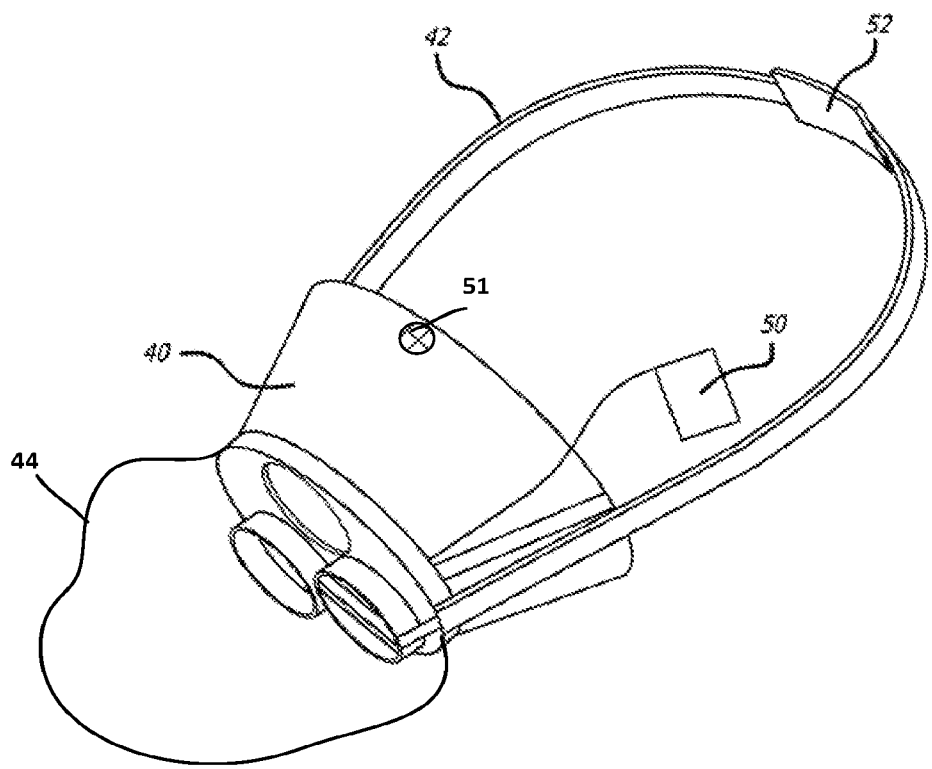
FIG. 2A is a perspective view of a mask including a strap and a set of sensors according to an example.
Figure 2B:
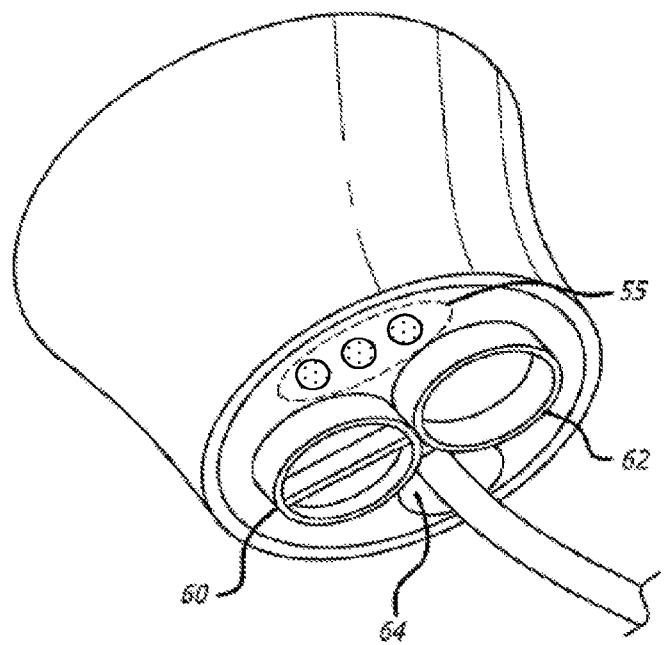
FIG. 2B is a perspective view of a mask including a set of indicators and a set of valves according to an example.

The PSOD system 100 includes a mask adapted to fit over the mouth and nose of the wearer, which can be tailored to a type of wearer including a pilot, a passenger, and a medical passenger or a patient. The mask can include a strap 42 that is configured to secure the mask to the wearer. The strap 42 of the mask may include a strap sensor 52 that is configured to be in contact with the wearer's neck. The strap sensor can be configured to get a measurement from capillaries on a cheek of the wearer. The strap 42 can be adjustable and elastic and can include wiring to connect the strap sensor 52 to the controller 130. One or more integrated mask sensors 51 can be integrated on the mask such as on a bridge of the wearer's nose and supported by a clamp (not shown) to provide a secure fit to the wearer (see FIGS. 2B and 2C). In addition, the sensor can be an auxiliary sensor 50 such as a fingertip sensor or an earlobe sensor that can be configured to provide the wearer's blood oxygen saturation level to the controller 130 according to an example.

Figure 2C:
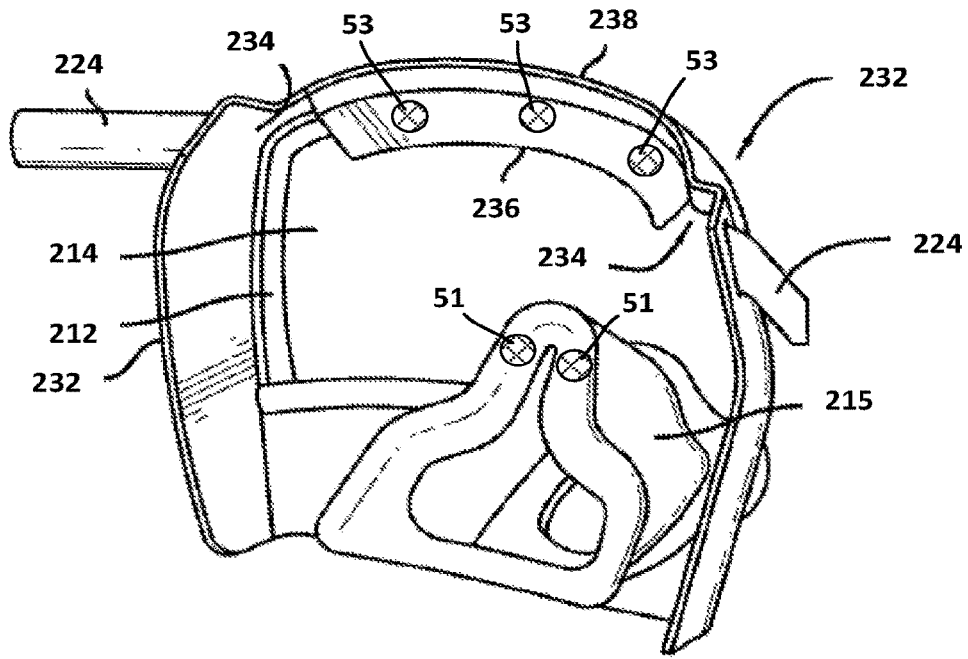
FIG. 2C is a perspective view of a mask configured for a pilot including a set of sensors and a number of indicators according to an example.
Figure 2D:
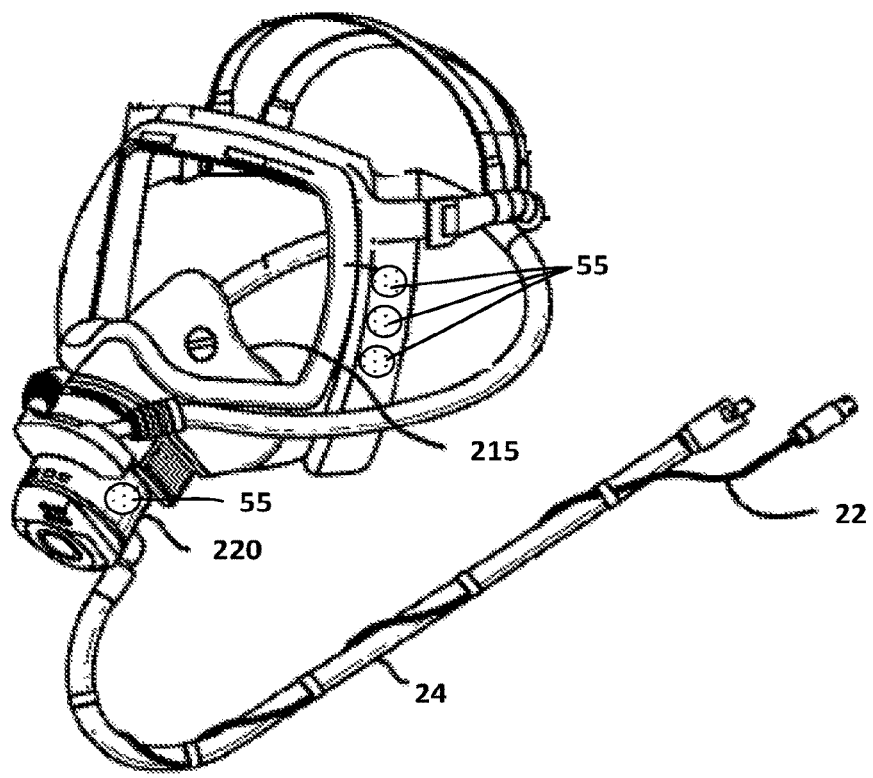
FIG. 2D is another perspective view of the mask of FIG. 2C showing a set of indicators according to an example.

FIGS. 2C and 2D illustrate an example of a mask that can be configured for supplying oxygen to a pilot of an airplane. An exemplary pilot mask is described in U.S. Pat. No. 8,028,700 by Hannah et. al., herein incorporated by reference in its entirety. However, it is contemplated that the mask described herein will optionally be worn without a flight helmet.

Referring to FIG. 2C, the pilot mask includes an elastic, flexible face seal or face piece 212, having a visor 214 in the face seal. The elastic face seal includes an oronasal cone 215 that seals around the nose and mouth of the wearer to provide the maximum required contaminant and leakage protection. Straps 224 can be connected to the face seal. The oxygen supply for the mask is provided by the tube 24. Electrical wiring 22 may be concurrently routed with the tube.

Flexible sealing flaps 232 are provided at selected points along the perimeter of the face seal to adapt the face seal of the mask to seal against the face of the wearer. The flexible sealing flaps are provided along the top, left and right sides of the face seal. The mask face piece also has two large sealing surfaces or channels 234 along each side of the mask that overlap and flex as necessary to adapt to a variety of exterior surfaces. As is illustrated in FIG. 2C, the top sealing flap 232 of the face seal includes an inner flap 236, adapted to form a seal along the forehead of the wearer, and an outer flap 238 for sealing along the helmet, that work together to seal the exposed face visible between the sides of the helmet. In one variant, the inner and/or outer flaps of the top flexible sealing flap, as well as the left and right side flexible sealing flaps, may include one or more internal chambers that may be connected to the regulator so as to be at least partially inflatable to enhance the sealing properties of the sealing flaps.

In the PSOD system, the pilot mask can further include a number of sensors 53 that are integrated into a forehead or eyebrow seal area according to an example (See FIG. 2C). The plurality of sensors may enhance data collection and accuracy. The controller may average the values collected by the three sensors 53 to determine a more accurate reading of the oxygen saturation, pulse or respiration rate of the wearer. The two sensors 51 may also be averaged to arrive at a nasal area reading for saturation, pulse or respiration rate of the wearer. The controller may correct for modality differences, as by adjusting the readings from sensors 51 to adjust for the fact that the tissue around the nasal area is of a different thickness than that around the brow line. The controller may then average the corrected or adjusted numbers from sensors 53 and sensors 51 and/or may preferentially use data from sensors 53 or 51 over the other based on a determination that one is likely to be more reliable than the other. For instance, the controller may determine that the forehead sensor data varies too significantly over time and thus is not likely indicative of the wearer's actual oxygen saturation, pulse or respiration rate. In that event the controller may use the correct or adjusted data from sensors 51 and discard or ignore the date from sensors 53, at least so long as the aberrations in the data from sensors 53 continue.

The pilot mask can include a set of indicators 55 that are configured to be visible to a co-pilot (See FIG. 2D). The indicators, in some examples, can be positioned on a headpiece and/or the regulator 220 portions of the pilot mask. Each indicator can be configured to reflect the pilot's health condition based on their oxygen saturation, pulse and/or breathing rate.

In an example, a PSOD system 100 is provided that is configured for supplying oxygen to one or more passengers on an airplane. The PSOD system 100 includes a mask configured to be released from an overhead storage compartment during a depressurization event (See FIG. 1B). The mask can be a frusto-conical thin walled structure providing an airtight seal against the passenger's face.

In an example, a PSOD system is provided that is configured to be mobile such as in portable life support systems for supplying oxygen to a patient. The auxiliary sensor 50 such as a fingertip sensor or a sensor placed under the wearer's jaw can be used.

In an example, a PSOD system can also be used for supplying oxygen to a patient in any other scenarios where the surrounding oxygen is variable and pressurized.

In an example, the mask can include a reservoir bag 44, an inlet 64, an inhalation valve 60, and a dilution valve 62 which can serve to coordinate flow between the reservoir bag and the mask, as well as between the mask and the surroundings. The inhalation valve 60 is configured to confine the oxygen flowing into the reservoir bag while the wearer is exhaling, as well as during the post-expiratory pause. The inhalation valve 60 can also prevent flow from the mask into the reservoir bag. When the wearer inhales, the inhalation valve 60 opens to allow for the inhalation of the oxygen that has accumulated in the reservoir bag. Upon depletion of the accumulated oxygen, the dilution valve 62 can open to allow cabin air to be drawn into the mask 40. Continuing flow of oxygen into the reservoir bag and through the inhalation valve 60 into the mask is thereby diluted by the cabin air that is inhaled during the balance of the inhalation phase. During exhalation, the dilution valve 62 opens to allow a free flow from the mask into the surroundings while the inhalation valve 60 closes to prevent flow from the mask back into the reservoir bag. All valves remain closed during the post-expiratory pause while oxygen continues to flow into the reservoir bag.

The mask 40 preferably incorporates one or more indicators 55. An indicator can be an LED according to an example. Each indicator can indicate a status of the wearer and operation of the PSOD system 100. For example, when a red indicator is illuminated, it can indicate that the mask is not functioning; a yellow indicator can indicate that the mask is functioning, but its oxygen sensing capabilities are not active. This indication may be due to the fact that one or more sensors are not correctly receiving information from the wearer, or that the mask is not in use. A green indicator can indicate that the mask is being used correctly and that the PSOD system 100 is functioning correctly.

In addition, one or more indicators can be integrated or projected onto an instrument panel of the airplane (not shown) such that an alarm/notification of a co-pilot health condition, based on oxygen saturation, pulse and/or breathing rate, can be monitored by the pilot. Other indicators, arrangements, and alarms/displays are also contemplated that are consistent with the spirit of the invention.

In the PSOD system 100, oxygen flow is provided based on the wearer's blood oxygen saturation level, which is measured using one or more non-invasive sensor technologies. The blood oxygen saturation level of a wearer can be determined using one or more sensor types at one or more sensor locations. Each mask can include a number of sensors that can be configured for providing redundancy, reducing signal noise, averaging of sensor data, as well as comparing different sensor data based on the sensor technology. In an example, each sensor can be used to generate a series of blood saturation output values over a given period of time that are sequentially representative of the wearer's blood-oxygen saturation level.

In one embodiment the sensor is a pulse oximeter configured to detect the oxygen saturation of the arterial blood of the wearer. The pulse oximeter can be placed on a thin part of the wearer's body (e.g. fingertip, earlobe, or in the case of an infant, across a foot). The pulse oximeter can use red and infrared light frequencies to measure a ratio of saturated to unsaturated hemoglobin in a wearer's blood.

The sensor can be a capnometer configured to monitor the wearer's carbon dioxide concentrations in expired gases. The capnometer can also determine adequacy of ventilation and a breathing rate of the wearer. The capnometer can be configured to detect a percentage of carbon dioxide in exhaled breath of the wearer, which can be used to determine the oxygen saturation and breathing rate.

In selected embodiments the sensor is a T-stat® oximeter (Spectros Corporation, Campbell, Calif.) that is configured to determine a wearer's StO2 level by interpreting a color of the wearer's blood. By measuring the oxygen saturation even in the smallest capillaries, the T-stat oximeter can be configured to determine the oxygen level of a wearer without a pulse. The T-stat oximeter is a Visible Light Spectroscopy (VLS) system that monitors the blood-oxygen level in microvascular tissue. A T-stat oximeter can use wavelengths in a visible spectrum (e.g. green and blue) to detect the blood oxygen saturation level.

In certain embodiments the controller 130 is configured to utilize sensor data measured from the wearer, and by implementing a comparison or look-up table, adjust the flow of oxygen to correspond to a prescribed saturation level, based on a number of physiological criteria, as well as an aircraft altitude and cabin pressure to prescribe a target saturation level.

The controller 130 can be configured to control the oxygen flow control device 28 to set a fractional amount of oxygen passing through each flow tube that is to be delivered to the wearer based on the sensor data.

In an aspect, the controller can be configured to operate in an open loop operation until a feedback control operation is activated. The feedback control operation can be activated based on predetermined period of in-range readings according. For example, the controller can operate in an open loop fashion until the controller receives a predetermined number of readings over a predetermined period of time which are within a predetermined range which is considered indicative of actual physiological readings.

In another aspect, the controller can be configured to calculate a series of running averages based on the one or more sensors. In an example, the controller can be configured to detect and remove erroneous signals from the series of running averages. In an example, the controller can be configured to determine that the sensor data is erroneous based on sensor data from a different sensor.

The controller 130 can be a stand-alone processing device (e.g., microchip, system on a chip, processor, etc.) or part of another processing system such as an instrument panel control system. Likewise, functions of the controller 130 can be done by a single unit such as a microcontroller or by a distributed and/or hierarchical processing network. A single controller 130 may be dedicated to a particular oxygen delivery system (e.g., unit or mask) or control a set of oxygen delivery systems (e.g., a panel of mask corresponding to a row or section of passenger seats, etc.). The controller 130 can include a processor or circuitry for generating and adjusting a running average of the blood oxygen saturation level, and for generating an output signal that is a function of the running average. The processor can be configured to perform checks for identifying possibly invalid output signal values and being responsive to the blood oxygen saturation level output signal values for evaluating a series of the blood oxygen saturation level output signal values and, based on the evaluation, providing a processed output signal. In the event of error detection, optionally a substitute output signal can be generated for each of the possibly invalid output signal values thereby forming a sequence of valid output signals. The processor can be configured to perform signal artifact recognition for identifying possibly invalid output signal values, and for providing a sequence of valid output signal values, exclusive of the identified possibly invalid output signal values; and means for generating a running average of the sequence of valid output signal values and for providing the running average as the processed output signal.

Figure 3B:
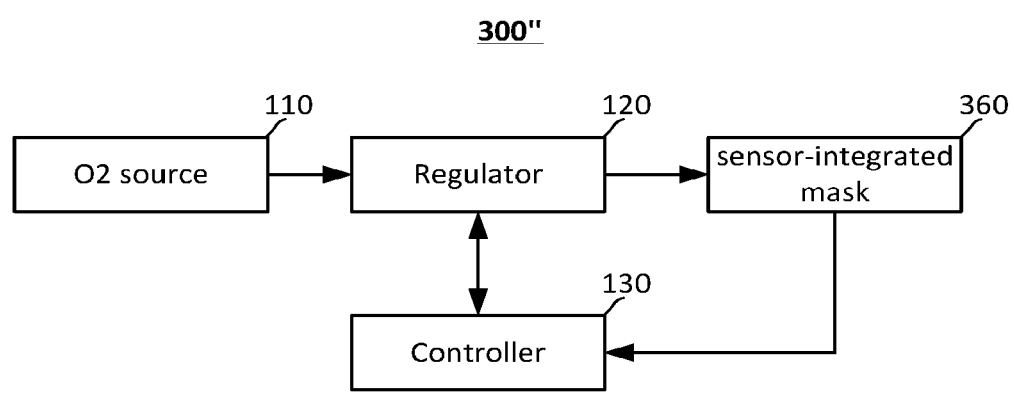
FIG. 3B is a schematic diagram of a pulse saturation oxygen delivery system including an oxygen source, a regulator, a controller, and a sensor-integrated mask according to an example.
Figure 3C:
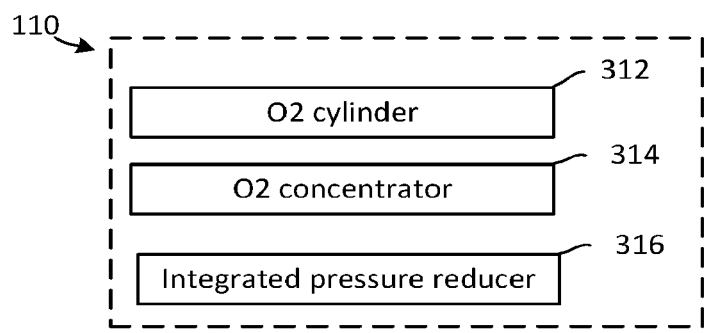
FIG. 3C shows examples of the oxygen source.
Figure 3D:
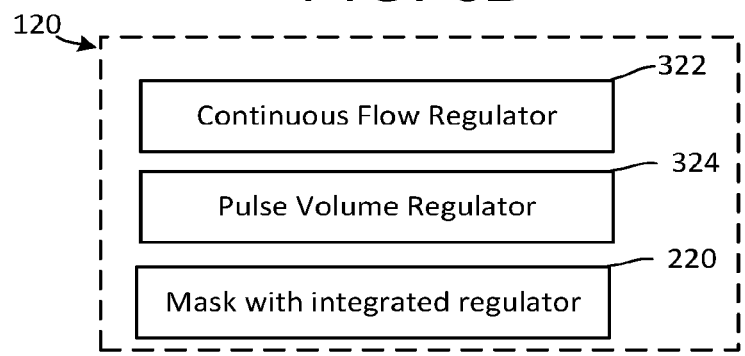
FIG. 3D shows examples of the regulator.
Figure 3E:
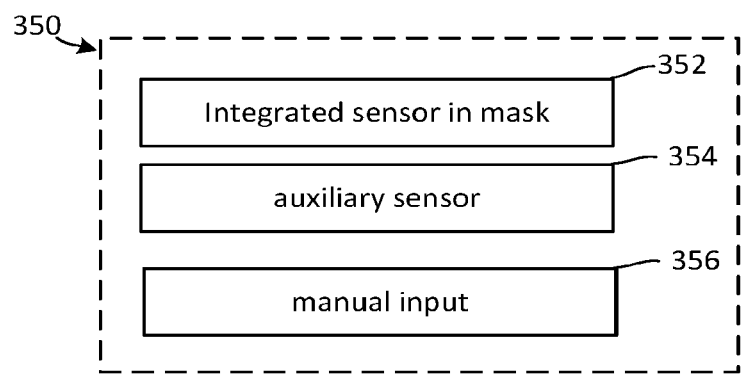
FIG. 3E shows examples of sources that can used to determine a wearer's blood oxygen saturation level.
Figure 4:
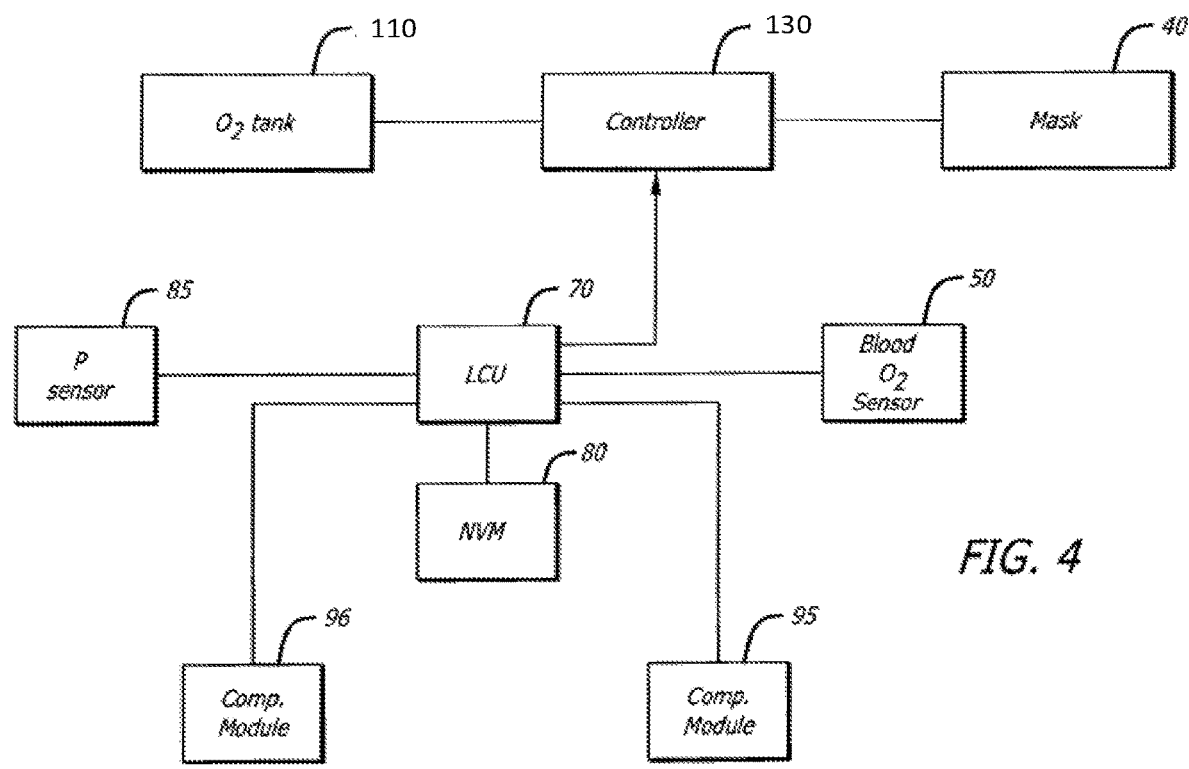
FIG. 4 is a schematic diagram of an alternate embodiment of the pulse saturation oxygen delivery system.
Figure 5:
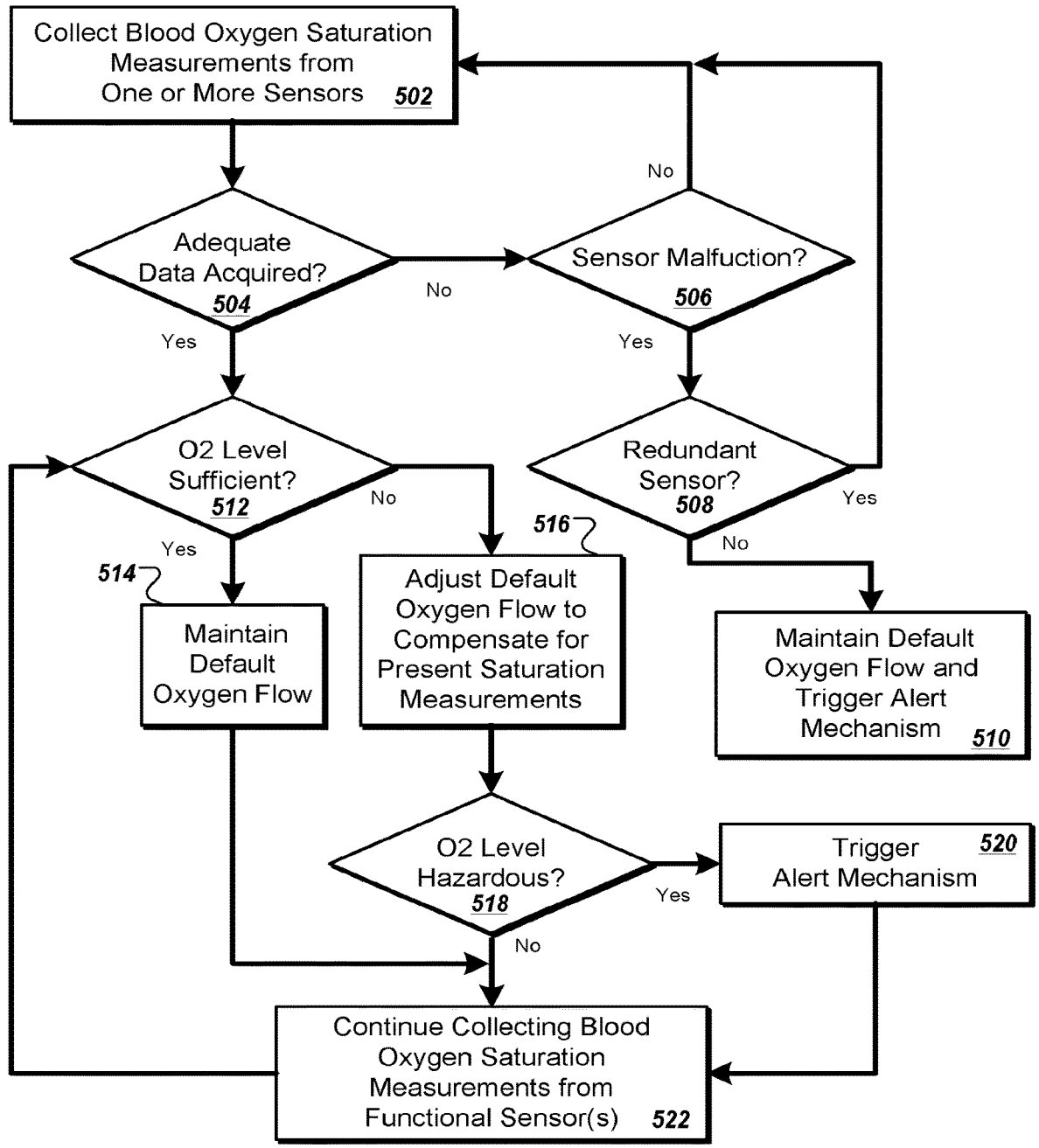
FIG. 5 is a flow chart describing a method for delivering oxygen through one or more masks on an airplane based on a wearer's blood oxygen saturation level.

As illustrated in FIG. 5A, a flow chart presents an example method 500 for delivering oxygen through one or more masks on an airplane based on a wearer's blood oxygen saturation level. The method 500, for example, may be performed by the controller 130 illustrated in FIGS. 3A, 3B, and 4.

In some implementations, the method 500 begins with collecting blood oxygen saturation measurements from one or more sensors for an initial collection period (502). The sensors, for example, may include any type of sensor described in relation to sensor 52 of FIG. 2A, sensors 51 and 53 of FIG. 2C, or sensors 350 of FIG. 3A, as well as sensors incorporated into the sensor-integrated mask 360 of FIG. 3B. In another example, a sensor can include manual input 356 via a panel 77 illustrated in FIG. 1B. The sensor data may be collected for at least a threshold period of time to establish a baseline average measurement of the wearer's blood oxygen saturation level. In a particular example, the sensor data may be collected for at least one minute. In another example, the sensor data may be collected for a shortened period of time (e.g., 10, 15, or 30 seconds, etc.) to confirm that all sensors appear to be functioning. In this manner, the wearer may be alerted at an earlier stage to reposition the mask and/or sensors. In a particular example, the controller 130 (described in relation to FIGS. 3A and 3B) may evaluate oximeter output signals communicated along the tubing 30 (illustrated in relation to FIG. 1B) from one or more sensors to the controller 130 and, based on the evaluation, determine a current blood oxygen saturation level.

In some implementations, at the end of the initial collection period it is determined whether adequate data has been acquired (504). In one example, a first portion of the data may have been collected prior to appropriate fixation of the sensor(s), causing partially inadequate data. In one example, adequate data may be identified by measurement of a blood oxygen saturation level at or beneath a threshold value (e.g., 90%, 80%, 70%, etc.). In another example, determination of inadequate data may be based upon erratic data points obtained from one or more of the sensor(s).

If it is determined that the inadequate data is not indicative of a sensor malfunction (506), in some implementations, the method 500 returns to collecting blood oxygen saturation measurements from the sensor(s) (502).

If, instead, it is determined that there is a sensor malfunction (506) providing inadequate data, in some implementations, it is determined whether there is a redundant operational sensor available (508). If there is a redundant operational sensor available (508), the method 500 may return to collecting blood oxygen saturation measurements from the redundant sensor(s) (502).

In some implementations, if no operational sensor is available (508), the default oxygen flow is maintained (510). For example, the oxygen flow may be based upon the altitude of the aircraft and/or a current cabin pressure. Further, in some embodiments, an alert mechanism may be triggered (510) to indicate sensor malfunction. For example, the visual indicators 55 described in relation to FIG. 2B or the visual indicators 55 of FIG. 2D may be lighted, a warning sound may be issued from a speaker in communication with the controller performing the method 500, and/or a trigger mechanism may be communicated to a separate system (e.g., cockpit console) for communication of an alert to a wearer or other crew member.

Alternatively, if adequate data has been acquired (504), in some implementations, the oxygen saturation level is analyzed to determine whether it is sufficient (512). In normal conditions, blood oxygen saturation levels in a healthy individual range around 95 to 100. In another example, maintaining a blood oxygen saturation level of about or above 90 may be considered beneficial to the health of the wearer of the oxygen mask. Insufficient measurements, for example, may be anything below 90.

In some implementations, if the blood oxygen saturation levels are determined to be sufficient (512), the default oxygen flow to the oxygen mask is maintained (514). As described above, the default oxygen flow may be based upon altitude of the aircraft and/or cabin pressure.

If, instead, it is determined that the blood oxygen saturation levels are insufficient (512), in some implementations, oxygen flow to the mask is adjusted to compensate for the present saturation measurements (516). For example, the oxygen flow rate may be calculated based upon the present blood oxygen saturation level in combination with the altitude of the aircraft and/or the cabin pressure. In another example, the default oxygen flow rate (e.g., based upon the altitude of the aircraft and/or the cabin pressure) may be adjusted based upon the present blood oxygen saturation level. The oxygen flow rate may be determined, in some examples, using an algorithm and/or a data look-up table.

In some embodiments, additional factors may be included in determining the adjusted oxygen flow rate such as, in some examples, i) a rate of change (e.g., decrease, increase) of blood oxygen saturation level, pulse or breathing rate over time, and/or ii) a range of blood oxygen saturation level (e.g., slightly below acceptable measurement, significantly below acceptable measurement, indicative of hazardous measurement, etc.), pulse or breathing rate. A hazardous measurement of blood oxygen saturation level, in one example, may be at or about 80%, while a measurement significantly below acceptable may be 81 to 85%, and a measurement slightly below acceptable may be in a range of 86 to 89%. More or fewer gradations may be used based upon particular implementation. Regarding physiological data, in some examples, breathing rate may be obtained from inspirations of a wearer of a pulse volume regulator and/or heart rate may be obtained from the one or more sensor or from a separate heart rate sensor, depending upon particular implementation. In a particular example, if the rate of blood oxygen saturation level over time is considered to be moderate to rapid and/or additional physiological data is indicative of a state of unwellness, the oxygen flow rate may be increase more dramatically than otherwise. Similarly, if the blood oxygen saturation level is increasing rapidly and moving close to an acceptable level, the oxygen flow rate may be decreased more dramatically (e.g., closer to the default rate). Upon determination of the adjusted rate, in a particular example, the controller 130 may issue a control signal to the oxygen flow control device 28 to deliver an additional dosage of oxygen to the wearer through a tubing (e.g., tubing 30 illustrated in FIG. 1B) to an oral-nasal mask, mask 40 (illustrated in FIGS. 2A and 2B), or pilot mask (illustrated in FIGS. 2C and 2D), depending upon the implementation.

In some implementations, if blood oxygen saturation levels are considered to be hazardous (518), an alert mechanism is triggered (520). As described in relation to step 510, visual indicators may be lighted, a warning sound may be issued from a speaker in communication with the controller performing the method 500, and/or a trigger mechanism may be communicated to a separate system (e.g., cockpit console) for communication of an alert to a wearer or other crew member. In a particular example, sensor malfunction may be relayed with a yellow visual indication on LEDs 55, while hazardous oxygen level may be relayed with a red visual indication on LEDs 55. The visual indication may flash, in some embodiments, to ensure immediate attention of nearby passengers and/or crew members.

In one implementation, the controller is coupled to the in-dash control instrumentation such that alerts concerning a pilot's saturation level, pulse or respiration rate are presented on the instrument panel to a co-pilot. In this manner the co-pilot may be alerted to a compromised health condition of the pilot without having seen the LEDs 55 on the pilots' mask.

In some implementations, whether or not the oxygen level was determined to be hazardous (518), the method 500 may continue collecting blood oxygen saturation measurements from any functional sensor(s) (522).

Although described in a particular order, on some implementations steps of the method 500 may be performed in a different order. For example, although continuing collection of blood oxygen saturation measurements (522) appears as a discrete step, it should be understood that, in many embodiments, the data would be continuously collected and analyzed. Further, in some implementations, more or fewer steps may be included in the method 500. For example, in some embodiments, if additional physiological data measurements are available (e.g., breathing rate obtained from inspirations of a wearer of a pulse volume regulator, heart rate from a heart rate sensor, etc.), even if the one or more sensors are inoperable for providing consistent blood oxygen saturation measurements, the method 500 may monitor and adjust based solely on that physiological data. For example, the oxygen flow may be adjusted in an effort to improve the condition of the wearer that is causing expression of the physiological symptom(s).

FIG. 4 schematically illustrates an embodiment of the PSOD system including non-volatile memory (NVM) 80 configured to store a first reference point, where the PSOD system can control the flow of air dilution from the cabin to the mask at a predetermined pressure or altitude above the first reference point. The PSOD system including NVM 80 may also include a logical control unit (LCU) 70 coupled to the NVM 80 and a pressure sensor 85, and configured for generating a control signal to regulate the supply of oxygen from the oxygen source and the flow of dilution air from the pressurized aircraft cabin via the regulator to the mask by processing the first reference point and the pressure data.

The NVM 80 in some applications can be a flash memory. Another option is for a serial port that is coupled to the LCU 70 for receiving the blood oxygen saturation level from the auxiliary sensor 50. The LCU 70 may include a first comparator module 95 that is configured to determine the corresponding altitude using a lookup table and a second comparator module 96 for generating the control signal based on a gauge setting (e.g. rotary displacement). The LCU 70 may also incorporate an amplifier for amplifying the control signal.

It will be apparent from the foregoing that while particular forms of the invention have been illustrated and described, various modifications can be made without departing from the spirit and scope of the invention. Accordingly, it is not intended that the invention be limited, except as by the appended claims. Obviously, numerous modifications and variations of the present invention are possible in light of the above teachings. It is therefore to be understood that within the scope of the appended claims, the invention may be practiced otherwise than as specifically described herein.

The invention claimed is:

1. A method for managing oxygen flow to an oxygen mask in a commercial passenger aircraft, comprising:
   collecting, from a plurality of sensors operatively connected to and integral with the oxygen mask, blood oxygen saturation measurements of a user of the oxygen mask, wherein the plurality of sensors comprises a first blood oxygen saturation sensor and a second blood oxygen saturation sensor, wherein at least one sensor of the plurality of sensors is disposed upon a strap of the oxygen mask such that the at least one sensor is configured to contact a cheek area of the respective user of the oxygen mask, wherein at least one sensor of the plurality of sensors is disposed upon a strap of the oxygen mask such that the at least one sensor is configured to contact a neck area of the respective user of the oxygen mask, and where at least one sensor of the plurality of sensors is disposed upon an interior surface of the oxygen mask such that the at least one sensor is configured to contact a bridge area of a nose of the user of the oxygen mask;
   determining, by the processing circuitry, the adequacy of the first blood oxygen saturation sensor;
   collecting, from the second blood oxygen saturation sensor of the oxygen mask, respective blood oxygen saturation measurements, in response to a determination that the first blood oxygen saturation sensor is inadequate;
   analyzing, by processing circuitry, the blood oxygen saturation measurements to determine a current oxygen saturation level;
   determining, by the processing circuitry, that the current oxygen saturation level is insufficient responsive to the current oxygen saturation level being less than a first threshold;
   adjusting, by the processing circuitry, an oxygen flow rate to the oxygen mask to an adjusted oxygen flow rate to compensate for the current oxygen saturation level being less than the first threshold;
   after adjusting the oxygen flow rate, continuing to collect, from the plurality of sensors, additional blood oxygen saturation measurements;
   analyzing, by the processing circuitry, the additional blood oxygen saturation measurements to determine an updated oxygen saturation level is hazardous to the user responsive to the updated oxygen saturation level being less than a second threshold, the second threshold less than the first threshold; and
   triggering, by the processing circuitry, an alert responsive to the updated oxygen saturation level being less than the second threshold.

2. The method of claim 1, wherein adjusting the oxygen flow rate comprises determining the adjusted oxygen flow rate based on the current oxygen saturation level and an altitude of the aircraft.

3. The method of claim 2, wherein the oxygen mask is a pilot mask worn by a pilot of the aircraft.

4. The method of claim 2, wherein the adjusted oxygen flow rate is based further on at least one physiological criteria of the user.

5. The method of claim 4, wherein the at least one physiological criteria comprises at least one of a pulse of the user and a breathing rate of the user.

6. The method of claim 1, wherein adjusting the oxygen flow rate comprises determining the adjusted oxygen flow rate based in part upon a rate of change of blood oxygen level in the user monitored over a period of time.

7. The method of claim 1, wherein triggering the alert comprises lighting at least one visual indicator upon an exterior surface of the oxygen mask.

8. An oxygen delivery system for use in a commercial passenger aircraft, comprising:
at least one oxygen mask comprising a plurality of blood oxygen saturation sensors including a first blood oxygen saturation sensor and a second blood oxygen saturation sensor, wherein at least one sensor of the plurality of sensors is disposed upon a strap of a first oxygen mask of the at least one oxygen mask such that the at least one sensor is configured to contact a cheek area of a respective user of the first oxygen mask, wherein at least one sensor of the plurality of sensors is disposed upon a strap of the first oxygen mask such that the at least one sensor is configured to contact a neck area of the respective user of the first oxygen mask, and where at least one sensor of the plurality of sensors is disposed upon an interior surface of the first oxygen mask such that the at least one sensor is configured to contact a bridge area of a nose of the respective user of the first oxygen mask;
at least one regulator; and
processing circuitry configured to control an oxygen flow rate from the at least one regulator to the at least one oxygen mask;
wherein controlling the flow of oxygen comprises
collecting, from the first blood oxygen saturation sensor of each oxygen mask of the at least one oxygen mask, respective blood oxygen saturation measurements;
determining, by the processing circuitry, the adequacy of the first blood oxygen saturation sensor;
collecting, from the second blood oxygen saturation sensor of each oxygen mask of the at least one oxygen mask, respective blood oxygen saturation measurements, in response to a determination that the first blood oxygen saturation sensor is inadequate;
analyzing, by processing circuitry, the respective blood oxygen saturation measurements corresponding to each mask of the at least one oxygen mask to determine a current oxygen saturation level of a user of the respective oxygen mask;
determining, by the processing circuitry, the current oxygen saturation level of a user of the first oxygen mask of the at least one oxygen mask is insufficient by comparison with a first threshold value or hazardous by comparison with a second threshold value less than the first threshold value; and
adjusting, by the processing circuitry based on the current oxygen saturation level and an altitude of the aircraft, an oxygen flow rate to at least the first oxygen mask to an adjusted oxygen flow rate to compensate for the current oxygen saturation level.

9. The oxygen delivery system of claim 8, wherein adjusting the oxygen flow rate comprises issuing a control signal to the regulator to deliver an additional fractional amount of oxygen.

10. The oxygen delivery system of claim 8, wherein collecting the respective blood oxygen saturation measurements comprises;
collecting the respective oxygen saturation for a threshold period of time; and
determining, based upon the respective oxygen saturation measurements, a baseline average oxygen saturation level of the user of the respective oxygen mask.

11. The oxygen delivery system of claim 8, wherein:
the first oxygen mask is an oral-nasal mask; and
the first blood oxygen saturation sensor of the plurality of blood oxygen saturation sensors of the first oxygen mask is a capnometer configured to monitor carbon dioxide concentrations in gases expired by the user of the first oxygen mask.

12. The oxygen delivery system of claim 8, wherein determining the adequacy of the first blood oxygen saturation sensor comprises identifying measurements of blood oxygen saturation level at or below a threshold value.

13. A sensor-integrated pilot mask for use by a commercial aircraft pilot comprising:
a visor;
an oronasal cone;
an oxygen supply tube configured to deliver an oxygen flow from an external oxygen source to the oronasal cone of the pilot mask;
an electrical cabling disposed along the oxygen supply tube;
a face seal for sealing the pilot mask against a face of a user, comprising flexible sealing flaps along a left, right, and top of a perimeter of the face seal and a large sealing surface on each side of the pilot mask;
a plurality of sensors, including a first blood oxygen saturation sensor and a second blood oxygen saturation sensor, the first and second oxygen saturation sensors being disposed upon an interior surface of the face seal and configured to remain substantially in contact with the face of the user during wear, wherein the second blood oxygen saturation sensor is configured to collect signals indicative of blood oxygen saturation level in response to a determination that the first blood oxygen saturation sensor is inadequate, and
wherein the plurality of sensors are configured to collect signals indicative of blood oxygen saturation level and to communicate the signals via the cabling, wherein the face seal includes an upper portion configured to seal against a forehead region of the face of the user, at least one sensor of the plurality of sensors is disposed upon the upper portion and configured to contact the forehead region, wherein the face seal includes an oronasal portion configured to seal around a mouth and nose region of the face of the user wherein at least one sensor of the plurality of sensors is disposed upon the oronasal portion and configured to contact a bridge of the nose of the user, wherein at least one sensor of the plurality of sensors is disposed upon a strap of the pilot mask such that the at least one sensor is configured to contact a neck area of the user of the pilot mask.

14. The sensor-integrated pilot mask of claim 13, further comprising at least one indicator lamp disposed upon an exterior surface of the pilot mask and configured for visibility to a co-pilot to present an alert associated with blood oxygen saturation level, wherein the at least one indicator lamp is configured to illuminate based upon at least one alert signal provided via the cabling.

15. The sensor-integrated pilot mask of claim 14, further comprising a regulator disposed between the oronasal cone and the oxygen supply tube, wherein a first indicator lamp of the at least one indicator lamp is positioned upon the regulator.

16. The sensor-integrated pilot mask of claim 14, wherein the plurality of sensors comprises at least one oximeter.

* * * * *